US00PP14999P2

(12) United States Plant Patent
Heffner

(10) Patent No.: US PP14,999 P2
(45) Date of Patent: Jul. 6, 2004

(54) PETUNIA PLANT NAMED 'BODTRUBLUICE'

(50) Latin Name: *Petunia×hybrida*
Varietal Denomination: Bodtrubluice

(75) Inventor: Michael R. Heffner, Santa Barbara, CA (US)

(73) Assignee: John Bodger & Sons Co., South El Monte, CA (US)

( * ) Notice: Subject to any disclaimer, the term of this patent is extended or adjusted under 35 U.S.C. 154(b) by 0 days.

(21) Appl. No.: 10/666,276

(22) Filed: Sep. 17, 2003

(51) Int. Cl.[7] ..... A01H 5/00
(52) U.S. Cl. ..... Plt./356
(58) Field of Search ..... Plt./356

*Primary Examiner*—Kent Bell
*Assistant Examiner*—Susan B. McCormick-Ewoldt
(74) *Attorney, Agent, or Firm*—C. A. Whealy

(57) ABSTRACT

A new and distinct cultivar of Petunia plant named 'Bodtrubluice', characterized by its mounded and trailing plant habit; freely branching habit; and numerous large and ruffled violet-colored flowers with darker violet-colored venation.

1 Drawing Sheet

Botanical classification: *Petunia×hybrida* cultivar Bodtrubluice.

BACKGROUND OF THE INVENTION

The present Invention relates to a new and distinct cultivar of Petunia plant, botanically known as *Petunia×hybrida*, and hereinafter referred to by the cultivar name Bodtrubluice.

The new Petunia is a product of a planned breeding program conducted by the Inventor in Lompoc, Calif. The objective of the breeding program is to create trailing Petunias with numerous large flowers and attractive flower coloration.

The new Petunia originated from a cross-pollination made by the Inventor in September, 1998 of a proprietary Petunia selection identified as 9P5251-8, not patented, as the female, or seed, parent, with a proprietary Petunia selection identified as 8P2004, not patented, as the male, or pollen parent. The new Petunia was selected as a single plant from the resulting progeny of the cross-pollination by the Inventor in a controlled environment in Lompoc, Calif.

Asexual reproduction of the new cultivar by vegetative cuttings taken in Lompoc, Calif. since June, 2000 has shown that the unique features of this new Petunia are stable and reproduced true to type in successive generations.

SUMMARY OF THE INVENTION

Plants of the cultivar Bodtrubluice have not been observed under all possible environmental conditions. The phenotype may vary somewhat with variations in environment such as temperature and light intensity without, however, any variance in genotype.

The following traits have been repeatedly observed and are determined to be the unique characteristics of 'Bodtrubluice'. These characteristics in combination distinguish 'Bodtrubluice' as a new and distinct cultivar:

1. Mounded and trailing plant habit.
2. Freely branching habit.
3. Numerous large and ruffled violet-colored flowers with darker violet-colored venation.

Compared to plants of the female parent, plants of the new Petunia have a more mounded habit and larger flowers. Compared to plants of the male parent, plants of the new Petunia are more vigorous and have a more mounded plant habit.

Plants of the new Petunia can be compared to plants of the cultivar Surfinia Blue Veined, not patented. In side-by-side comparisons conducted in Lompoc, Calif., plants of the new Petunia differed from plants of the cultivar Surfinia Blue Veined in the following characteristics:

1. Plants of the new Petunia were more mounded than plants of the cultivar Surfinia Blue Veined.
2. Plants of the new Petunia had larger flowers than plants of the cultivar Surfinia Blue Veined.
3. Plants of the new Petunia flowered under short day conditions whereas plants of the cultivar Surfinia Blue Veined did not flower under short day conditions.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Petunia. The photograph at the top of the sheet comprises a side perspective view of a typical flowering plant of 'Bodtrubluice' grown in a container. The photograph at the bottom of the sheet comprises a close-up view of typical flower buds, developing flowers, open flowers and the upper and lower surfaces of typical leaves of 'Bodtrubluice'.

DETAILED BOTANICAL DESCRIPTION

The aforementioned photographs and following observations and measurements describe plants grown in Lompoc, Calif., under commercial practice during the summer in a polycarbonate-covered greenhouse with day temperatures about 21 to 27° C., night temperatures about 16 to 18° C. and light levels about 5,000 to 9,000 foot-candles. Plants were grown with one rooted cutting per 15.25-cm container for about 11 weeks. In the following description, color references are made to The Royal Horticultural Society Colour Chart, 1995 Edition, except where general terms of ordinary dictionary significance are used.

Botanical classification: *Petunia×hybrida* cultivar Bodtrubluice.

Parentage:

*Female parent.*—Proprietary Petunia selection identified as 9P5251-8, not patented.

*Male parent.*—Proprietary Petunia selection identified as 8P2004, not patented.

Propagation:

*Type cutting.*—Vegetative cuttings.

*Time to initiate roots.*—About 7 to 10 days at 27° C.

*Time to develop roots.*—About 28 to 42 days at 18 to 24° C.

*Root description.*—Fine, fibrous, whitish in color.

*Rooting habit.*—Freely branching.

Plant description:

*Form.*—Annual flowering plant; indeterminate; initially upright, then mounded and outwardly spreading to low trailing; plants eventually becoming roughly hemispherical in shape. Vigorous growth habit. Freely basal branching with about 8 main lateral branches per plant with lateral branches potentially forming at every node.

*Usage.*—Appropriate for hanging baskets, window boxes, patio containers and landscape applications.

*Plant height.*—About 16 cm.

*Plant diameter.*—About 55 cm.

*Lateral branches.*—Length: About 30 cm. Diameter: About 6 mm. Internode length, vegetative shoots: About 2.5 to 3 cm. Internode length, flowering shoots: About 5 cm. Texture: Pubescent. Color: 144B.

*Foliage description.*—Arrangement, before flowering: Alternate, simple. Arrangement, when flowering: Opposite, simple. Length: About 5.5 cm. Width: About 5 cm. Shape: Oval to elliptical. Apex: Broadly acute. Base: Attenuate. Margin: Entire. Texture, upper and lower surfaces: Glandular, viscid; pubescent. Venation pattern: Pinnate, arcuate. Color: Developing foliage, upper surface: 138A. Developing foliage, lower surface: 143B. Fully expanded foliage, upper surface: 138A. Fully expanded foliage, lower surface: 143A. Venation, upper surface: 144C. Venation, lower surface: 143B. Petiole length: About 1 cm. Petiole diameter: About 6 mm. Petiole color: 144C.

Flower description:

*Flower type and habit.*—Large salverform flowers; flowers face upward or outward; single, axillary. Flowers persistent. Freely flowering, typically about 80 open flowers and flower buds per plant at one time.

*Natural flowering season.*—Long day responsive; spring until frost in the autumn; flowering continuous during the flowering period. Plants of the new Petunia will also flower under short day conditions.

*Flower longevity on the plant.*—About 4 to 5 days.

*Fragrance.*—Faint; sweet.

*Flower size.*—Diameter: About 7.5 cm. Tube length: About 3 to 3.5 cm. Throat diameter, distal end: About 1.6 cm. Tube diameter, proximal end: About 6 mm.

*Flower buds.*—Length: About 5 cm. Diameter: Apex: About 2 cm. Base: About 1 cm. Shape: Elongated oblong with ruffled apices. Color: 90D.

*Corolla.*—Arrangement/appearance: Single whorl of five petals, fused into flared trumpet with distinct clefts between petal lobes. Petal length from throat: About 3.2 cm. Petal width: About 4.5 cm. Petal shape: Roughly spatulate or fan-shaped. Petal apex: Rounded with slight emargination. Petal margin: Entire, ruffled. Petal texture: Smooth, velvety. Color: Petal, upper surface, when opening: Initially 157A, then becoming closer to 85D. Petal, lower surface, when opening: Towards margins, 85B, towards centers, 155A. Petal, upper surface, fully opened: 88A to 88B; color becoming closer to 91B to 91C with development. Petal, lower surface, fully opened: Towards margins, 86B to 86C, towards centers, 88D. Flower throat (inside): 79A. Flower tube (outside): 83B. Venation, upper petal surface: 89A to brighter than 89A. Venation, lower petal surface: 146D. Venation, throat: 79A. Venation, tube: 146D.

*Sepals.*—Arrangement/appearance: Single whorl of five sepals fused at base, star-shaped. Length: About 2 cm. Width: About 1.5 cm. Shape: Rounded elliptic. Apex: Broadly acute. Margin: Entire. Texture, upper and lower surfaces: Glandular, viscid. Color, upper surface: 147A. Color, lower surface: 146B.

*Peduncles.*—Length: About 3 cm. Width: About 1.5 mm. Angle: About 45° to the stem. Strength: Strong. Texture: Pubescent. Color: 146C.

*Reproductive organs.*—Stamens: Quantity/arrangement: Five, adnate to corolla tube. Anther shape: Ovoid. Anther length: About 1.5 mm. Anther color: 97A. Pollen amount: Sparse. Pollen color: 97A. Pistils: Quantity: One. Pistil length: About 2.7 cm. Stigma shape: Rounded, flattened. Stigma color: 146A. Style length: About 2 cm. Style color: 145C. Ovary color: 145A.

*Fruit/seed.*—Fruit and seed production has not been observed.

Disease/pest resistance: Plants of the new Petunia have not been noted to be resistant to pathogens and pests common to Petunia.

It is claimed:

1. A new and distinct cultivar of Petunia plant named 'Bodtrubluice', as illustrated and described.

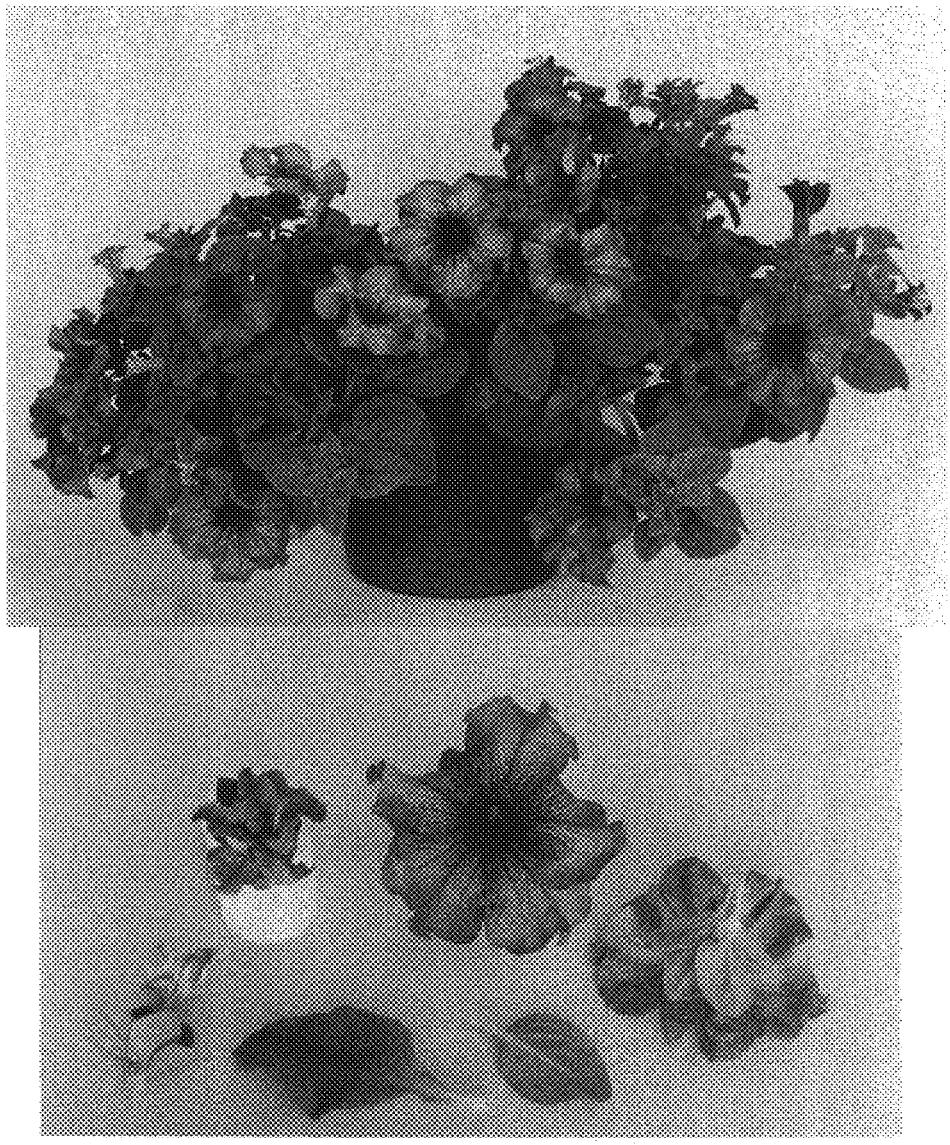

* * * * *